United States Patent [19]

Schick

[11] Patent Number: 5,419,208

[45] Date of Patent: May 30, 1995

[54] MULTIPORT SELECTION VALVE

[75] Inventor: Hans G. Schick, Anacortes, Wash.

[73] Assignee: Upchurch Scientific, Inc., Oak Harbor, Wash.

[21] Appl. No.: 10,814

[22] Filed: Jan. 29, 1993

[51] Int. Cl.⁶ .................... G01N 30/24; F16K 5/04; F16K 11/085

[52] U.S. Cl. ............... 73/863.73; 73/864.84; 73/61.55; 73/61.56; 137/625.17

[58] Field of Search ............... 73/61.55, 61.56, 863.31, 73/863.32, 863.33, 863.71, 863.72, 863.73, 864.81–864.87; 422/70; 137/625.17, 625.41, 602, 893, 605, 606, 607; 251/208, 209, 309, 310, 311, 312

[56] References Cited

U.S. PATENT DOCUMENTS

| | | | |
|---|---|---|---|
| 3,080,759 | 3/1963 | McQuaid | 73/863.73 |
| 3,475,950 | 11/1969 | Ferrin | 73/863.73 |
| 3,531,084 | 9/1970 | Hendrix | 251/314 |
| 3,559,458 | 2/1971 | Hrdina | 73/61.56 X |
| 3,653,594 | 4/1972 | Bok et al. | 137/625.41 X |
| 3,681,998 | 8/1972 | Karas et al. | 73/863.73 |
| 3,831,621 | 8/1974 | Anthony et al. | 137/625.31 X |
| 3,847,546 | 11/1974 | Paul | 73/23.35 X |
| 3,916,692 | 11/1975 | Abrahams et al. | |
| 3,918,913 | 11/1975 | Stevenson et al. | 141/130 |
| 3,961,534 | 6/1976 | Gundelfinger | |
| 3,989,025 | 11/1976 | Franco | 123/190.6 |
| 4,068,528 | 1/1978 | Gundelfinger | |
| 4,158,630 | 6/1979 | Stearns | 210/198 C |
| 4,182,184 | 1/1980 | Bakalyar et al. | |
| 4,196,654 | 4/1980 | Stearns | 92/33 |
| 4,222,412 | 9/1980 | Carle | 137/625.47 |
| 4,242,909 | 1/1981 | Gundelfinger | |
| 4,393,726 | 7/1983 | Tamm et al. | 73/864.84 |
| 4,444,066 | 4/1984 | Ogle et al. | 73/863.72 |
| 4,550,742 | 11/1985 | Stearns | 137/14 |
| 4,632,150 | 12/1986 | Gagas | 137/625.29 X |
| 4,655,095 | 4/1987 | Russo et al. | 73/864.83 |
| 4,722,830 | 2/1988 | Urie et al. | 73/863.73 |
| 4,726,238 | 2/1988 | Reese et al. | 73/864.83 |
| 5,193,581 | 3/1992 | Shiroto et al. | 137/625.11 |

FOREIGN PATENT DOCUMENTS 208560 8/1990 Japan .................... 73/61.56

OTHER PUBLICATIONS

1989 *Cheminert* cataglog, pp. 3 and 6–11, published by Valco Instruments, Inc. in the U.S.A.
1990 *Victrex Peek* brochure, p. 46, published by ICI in the U.S.A.
1991 *Alltech catalog*, pp. 614 and 619, published by Alltech Associates, Inc. in the U.S.A. Catalog No. 250.
1991 *Bodman* catalog, p. 116, published by Bodman in the U.S.A.
1992 *Hamilton* catalog, pp. 72–74, published by Hamilton Co. in the U.S.A.
1992 *Chrom Tech* catalog, pp. 205 and 208, published by Chrom Tech, Inc. in the U.S.A.
L. R. Snyder and J. J. Kirkland book *Introduction to Modern Liquid Chromatography* (2d ed. 1979), chapters 2, 4 and 5 (pp. 15–82, 125–167, & 168–245).

*Primary Examiner*—Thomas P. Noland
*Attorney, Agent, or Firm*—Vinson & Elkins

[57] ABSTRACT

A multiport selection valve which is biocompatible and can be used at pressures of up to 2000 psi is described. A housing made of a polymer such as polyetheretherketone has a plurality of selection ports and a common port. Located within the housing and the end at which the ports are located is a rotor seal. Located within and adjacent to the rotor seal is a rotor tip. The rotor tip has a passageway therethrough to allow fluid communication between the desired selection port and the common port. In the preferred embodiment of the invention, the housing rotor seal and the rotor tip are made of synthetic polymers which are biocompatible. The valve also includes a rotor to which a knob is attached, thus allowing an operator to select a particular selection port. In an alternative embodiment, the valve of the present invention can be attached to a bulkhead and an actuator, thereby allowing automatic operations in accordance with programmed instructions.

24 Claims, 5 Drawing Sheets

MULTIPORT SELECTION VALVE

FIELD OF THE INVENTION

This invention relates generally to a multiport selection valve which allows an operator to select which of several streams should be connected to a common port. More particularly, this invention relates to a multiport selection valve useful in liquid chromatography applications.

BACKGROUND OF THE INVENTION

Liquid chromatography (LC) is a well-known technique for separating the constituent elements in a given sample. A typical liquid LC system has a sophisticated plumbing system utilizing tubing to transfer fluid between the various components of the LC system. Various fittings are used to connect the tubing to these components. Many different types of LC systems and components for LC systems are commercially available from a number of vendors. For example, Millipore Corporation of Milford, Mass., Beckman Instruments of Fullerton, Calif., and Hewlett-Packard Company of Palo Alto, Calif., all sell LC systems, including pumps, sample injection valves, columns, and detectors, among other things.

In a typical LC system, a liquid solvent (often called the "mobile phase") is introduced from a solvent reservoir and delivered via tubing to the pump. In operation, the pump creates a vacuum which draws the solvent through the tubing and into the pump. The solvent exits the pump under a higher pressure and then passes to the sample injection valve. As the name suggests, the sample injection valve allows an operator to inject a sample into the LC system, where the sample will be carried along with the mobile phase.

After the sample injection valve, most LC systems include a column. A typical column usually consists of a piece of steel tubing which has been packed with a "packing" material. The "packing" consists of the particulate material inside the column. This material is usually made of silica- or polymer-based particles, which are often chemically bonded with a chemical function. When the sample is carried through the column (along with the mobile phase), the various components (solutes) in the sample migrate through the packing within the column at different rates (i.e., there is differential migration of the solutes). Because of the different rates of movement, the components gradually separate as they move through the column. A more detailed description of the separation process can be found, among other places, in Chapters 2 and 5 of *Introduction to Modern Liquid Chromatography* (2d ed. 1979) by L. R. Snyder and J. J. Kirkland, which chapters are incorporated by reference herein.

Once the sample (with its components now separated) leaves the column, it flows with the mobile phase past a detector. The detector detects the presence of specific molecules or compounds. As discussed in Chapter 4 of *Introduction to Modern Liquid Chromatography*, which chapter is incorporated by reference herein, two general types of detectors are used in LC applications. One type measures a change in some overall physical property of the mobile phase and the sample (such as their refractive index). The other type measures only some property of the sample (such as the absorption of ultraviolet radiation). In essence, a typical detector in an LC system can measure and provide an output in terms of mass per unit of volume (such as grams per milliliter) or mass per unit of time (such as grams per second) of the sample's components. From such an output signal, a "chromatograph" can be provided; the chromatograph can then be used by an operator to determine the chemical components present in the sample.

Figure 1:
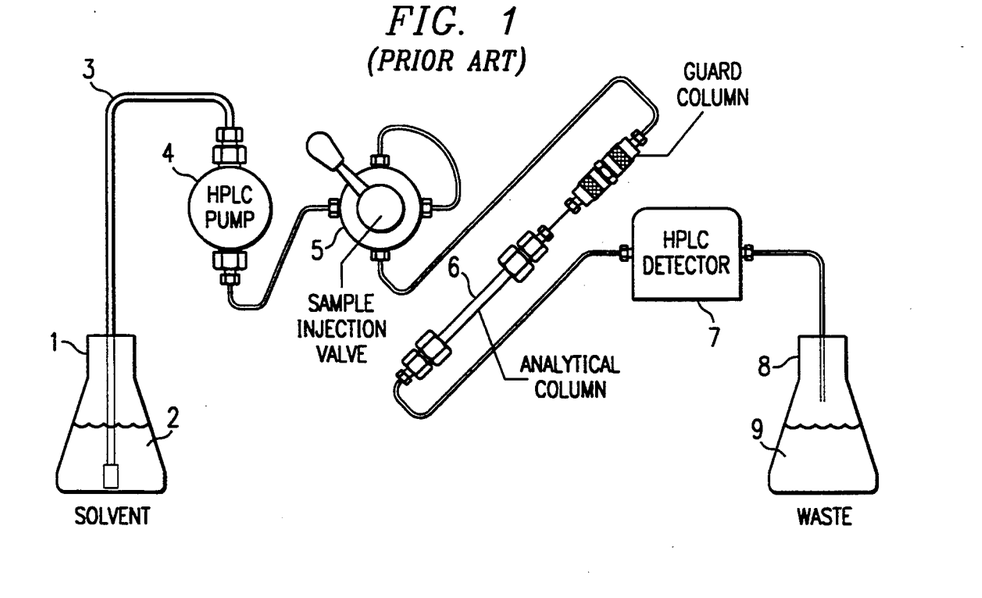
FIG. 1 is a schematic diagram of the typical components in an LC system.

In FIG. 1, a block diagram illustrating the typical environment in which the present invention will be utilized is provided, with the basic and essential elements of a prior art LC system shown. A reservoir 1 contains a solvent or mobile phase 2. Tubing 3 connects the mobile phase 2 in the reservoir 1 to a pump 4. The pump 4 is connected via tubing to a sample injection valve 5 which, in turn, is connected via tubing to a first end of a column 6. The second end of the column 6 is then connected via tubing to a detector 7. After passing through the detector 7, the mobile phase 2 and the sample injected via injection valve 5 are transported via tubing into a second reservoir 8, which contains the chemical waste 9. As noted above, the sample injection valve 5 is used to inject a sample of a material to be studied into the LC system. In operation, the mobile phase 2 flows through the tubing 3, which is used to connect the various elements of the LC system together.

When the sample is injected via sample injection valve 5 in the LC system, the sample is carried by the mobile phase through the tubing into the column 6. As is well known in the art, the column 6 contains a packing material which acts to separate the constituent elements of the sample. After exiting the column 6, the sample (as separated via the column 6) then is carried to and enters a detector 7, which detects the presence or absence of various ions. The information obtained by the detector 7 can then be stored by well-known means (such as a personal computer programmed to do so) and used by an operator of the LC system to determine the constituent elements of the sample injected into the LC system.

In addition to the above components, many LC systems will include various filters, check valves, or the like in order to prevent contamination of the sample or damage to the LC system. It will be understood to those skilled in the art that, as used herein, the term "LC system" is intended in its broad sense to include all apparatus used in connection with liquid chromatography, whether made of only a few simple components or made of numerous, sophisticated components which are computer controlled or the like.

Because of the substantial amount of time and effort it often takes to set up and test a particular configuration of a LC system, a multiport selection valve is particularly useful. The use of appropriate multiport selection valves in an LC system allows the operator to design and configure a more comprehensive LC system which can use different mobile phases, different columns, and the like. Once plumbed, such a comprehensive LC system can be immediately used with a different column, for example, simply by using the appropriate multiport selection valve to switch the flow to the different column.

Most pumps used in the LC systems which are commercially available can generate relatively high pressures of up to around 10,000 to 15,000 psi. In many situations, an operator can obtain successful results by operating an LC system at low pressures of anywhere from just a few psi or so up to 1,000 psi or so. In other situations, however, an operator will find it desirable to operate an LC system at relatively "higher" pressures of over 1,000 psi. The operation and use of LC systems at such "higher" pressure levels is often referred to as "high pressure liquid chromatography" or "high performance liquid chromatography" (HPLC). In order to be suitable for HPLC applications, an LC component must be made to withstand the required pressures. Otherwise, the component may fail, thus potentially causing personal injury, the loss of valuable materials and research efforts, and the like. For these and other reasons, many components and fittings used in HPLC are made of stainless steel.

More recently, it has been realized that the use of stainless steel (and other metals) in the components of an LC system which come in contact with the mobile phase create potential drawbacks when dealing with biological samples. For example, the ions in a sample may attach themselves to the stainless steel material if the mobile phase comes in contact with the stainless steel. Similarly, ions from the metal components may detach and eventually flow past the detector, thus leading to potentially erroneous results. Hence, those portions of the LC components which come in contact with the mobile phase need to be biocompatible (i.e., chemically inert with respect to biological samples and the mobile phase carrying these samples) in many applications involving biological samples. Simply put, there is a need for biocompatible components of LC systems.

Generally speaking, multiport selection valves have been known for some time. The following is a brief summary of several earlier patents involving multiport selection valves. U.S. Pat. No. 3,961,534 describes a two-position rotary valve for injecting a sample into a LC system. This particular valve is switchable between a load position and an inject position. U.S. Pat. No. 4,158,630 describes an apparatus for delivering samples to a liquid chromatography system where the samples are loaded into sample loops via a loop selector valve. The loop selector valve includes a rotor which connects the inlet and outlet lines of the selected loop. In addition, a multiport valve which includes a stator and rotor assembly is used to selectively connect the various ports. This patent also mentions the use of an actuator motor to advance the valves automatically. U.S. Pat. Nos. 4,158,630 (Stearns) and 3,961,534 (Gundelfinger) are incorporated by reference herein as if fully set forth.

U.S. Pat. No. 4,444,066 describes a high pressure multiport valve for control of the injection of a sample into a liquid chromatography column. The valve operates in two positions and is said to require a minimum of movement between the two positions. In U.S. Pat. No. 4,655,095, a compound valve is described which can be used as a sample injector in a liquid chromatography system. The valve has a shaft including an axle bore on one end and a radial bore communicating with the axle bore. U.S. Pat. Nos. 4,444,066 (Ogle et al) and 4,655,095 (Russo et al) are incorporated by reference as if fully set forth herein.

In the past, multiport valves for high pressure LC applications were limited to valves made of metal or otherwise having metallic parts which contacted the mobile phase. Hence, such valves were not biocompatible. On the other hand, those multiport valves which were made of plastic materials (and were therefore biocompatible) could only be used at relatively low operating pressures; i.e., up to approximately 500 psi.

Hence, there is a need for a multiport selection valve which is biocompatible and which can be used in relatively high pressure applications (such as those up to 2,000 psi or so) without leaking or otherwise failing.

An object of the present invention is to provide an efficient, effective and inexpensive multiport selection valve which is biocompatible.

Another object of the present invention is to provide the flexibility of establishing leak free fluid communication between a common port to any one of a plurality of selection ports.

It is another object of the present invention to provide a multiport selection valve that is biocompatible and can be used at relatively higher pressures of up to around 2,000 psi in a liquid chromatography system.

It is yet another object of the present invention to provide a multiport selection valve which maintains a low dead volume while connecting a common port to one of a plurality of selection ports.

It is yet another object of the present invention to allow a different selection port to be selected with a minimum of torque.

The above and other advantages of the present invention will become readily apparent to those skilled in the art from the following detailed description of the present invention, and from the attached drawings, which are briefly described below.

SUMMARY OF THE INVENTION

The present invention provides an improved multiport selection valve for selectively connecting a common port to one of a plurality of selection ports to establish fluid communication therebetween. The present invention is particularly useful in liquid chromatography systems where it is desirable to have the flexibility to connect one of a number of destination tubes to a common source tube or alternatively from a number of source tubes to connect to a common destination tube.

The improved multiport selection valve utilizes a rotor tip having a passageway positioned so that a first end of the passageway remains aligned with a common port while the second end of the passageway is selectively aligned with any one of a plurality of selection ports. The multiport selection valve of the present invention allows a plurality of tubes which transport fluid to be connected to the common port and the corresponding plurality of selection ports. These fittings work in conjunction with a rotor seal to establish leak free operation of the multiport selection valve. The rotor and rotor tip are separate parts, although they can be combined into a single part in an alternative embodiment. When the body of the multiport selector valve, the rotor, and all other components which may come into contact with the mobile phase are made of polymeric or otherwise inert materials, the multiport selector valve is biocompatible. The rotor of the multiport selection valve of the present invention can be manually turned by a knob connected to the end of the rotor. In an alternate form of the present invention, the rotor of the multiport selector valve can be automatically controlled and turned by an electrical actuator connected to the end of the rotor and connected to a personal computer with preprogrammed instructions.

DESCRIPTION OF THE PREFERRED EMBODIMENT

Figure 2:
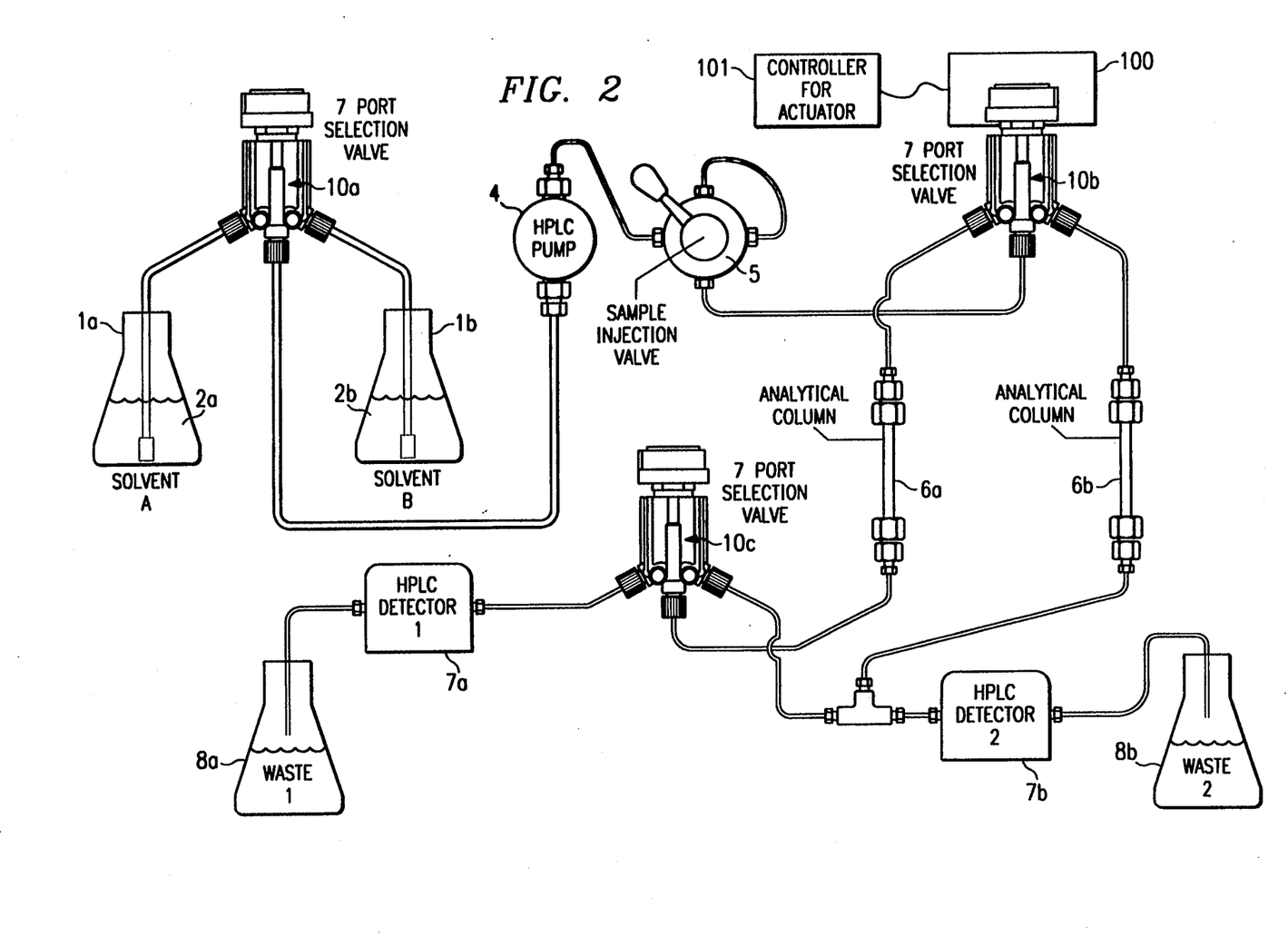
FIG. 2 is a schematic diagram illustrating common applications of a multiport selection valve of the invention within a typical LC system.

FIG. 2 illustrates a possible configuration of a LC system which includes multiport selection valves 10a, 10b, and 10c in accordance with the multiport selection valve 10 of the present invention described below. Two of the selection ports of the selection valve 10a are connected to two different reservoirs 1a and 1b, respectively. The common port of the valve 10a is then connected to the pump 4, thus allowing the operator to selectively choose between the mobile phases located in reservoirs 1a and 1b, respectively. A second multiport selection valve 10b is connected at its common port to the output of the sample injection valve 5. As shown, two of the selection ports of valve 10b connected to the input of the columns 6a and 6b, respectively. These connections thus allow an operator of the LC system shown in FIG. 2 to selectively direct the flow of the mobile phase and sample to one of the two different columns 6a and 6b for the separation of the sample into its constituent elements.

In FIG. 2, valve 10b is connected to an actuator 100 of a type known in the art. Actuator 100 can be a small motor attached to the valve 10b so as to automatically select between the selection ports of valve 10b. Actuator 100 is shown as connected to a controller 101, which can be a preprogrammed control device (such as a personal computer) of a type well known in the art. Controller 101 and actuator 100 thus provide for the automatic connection of the desired selection port of valve 10b.

As also shown in FIG. 2, yet a third multiport selection valve 10c is connected at its common port to the output of the column 6a. As shown, two of the selection ports of multiport selection valve 10c are connected to the inputs of two different detectors 7a and 7b, respectively, so as to allow an operator to selectively choose one of two different types of detectors 7a and 7b. As also shown in FIG. 2, the outputs of columns 7a and 7b are connected to two different waste receptacles 8a and 8b, respectively. As is well known to those skilled in the art, the various components of the LC system shown in FIG. 2 are connected with appropriate tubing, which in turn is attached to the respective components with appropriate fittings. Of course, it will be obvious to those skilled in the art that multiport selection valves utilizing the present invention can be used in much more complex LC systems in an almost unlimited number of permutations and combinations.

Figure 3:
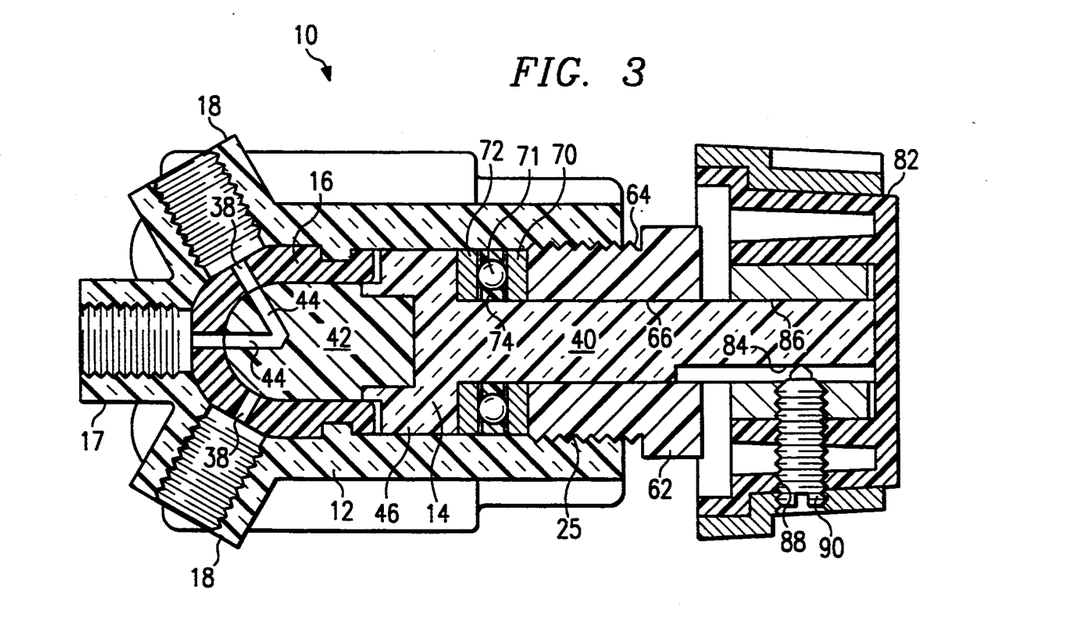
FIG. 3 is longitudinal sectional view of the multiport selection valve of the present invention.

Referring now to FIG. 3, the preferred embodiment of multiport selection valve 10 is shown. As shown, the valve 10 generally includes (among other things) a housing 12, a central rotatable rotor 14, a rotor seal 16, a rotor tip 42, a common port 17 and a plurality of selection ports 18. Positioned inside the housing 12 so that its front end is adjacent to the bottoms of common port 17 and the selection ports 18 is the rotor seal 16. As shown, the selection ports 18 are positioned around common port 17 in a radial, symmetrical fashion along a first end of the outside diameter of housing 12. Ports 17 and 18 in this embodiment are cylindrical in shape and include threaded grooves on their respective inner surfaces. The threads are provided so as to allow an operator to connect and secure tubing connections in the ports 17 and 18 (as described below in more detail).

In the preferred embodiment of the valve 10, there are six selection ports 18 located around the first end of the housing 12. However, it should be understood that there could be as few as two selection ports 18. Although additional selection ports 18 can be added, the number of selection ports 18 in a multiport selection valve 10 is generally limited by the diameter of each of the cylindrical selection ports 18 and also by the diameter of housing 12.

As shown in FIG. 3, the rotor tip 42 is located within the cup defined by the interior of the rotor seal 16. A first end of the rotor tip 42 is in the shape of a hemisphere, while its second end preferably consists of a hexagonal base so as to better mate with the front end of the rotor 14. (As described more fully below in connection with alternative embodiments of the present invention, the rotor tip 42 and the rotor 14 can be formed by a unitary piece. Alternatively, the rotor tip 42 can be a sphere which is removably attached to the rotor 14.) Rotor seal 16 has a plurality of passageways 38. The rotor seal 16 is positioned in the valve 10 so that the passageways 38 are located adjacent the holes at the bottoms of the common port 17 and the selection ports 18, thereby allowing fluid communication between the bottoms of the common and selection ports 17 and 18 and the interior of the rotor seal 16. Apart from such fluid communication as is allowed by passageways 38, however, the exterior surface of the rotor seal 16 forms a seal between itself and the interior surface of the housing 12. As also shown in FIG. 3, however, the rotor tip 42 has a passageway 44 therein. Where the rotor tip 42 is positioned within the interior of the rotor seal 16, and the passageway 44 is aligned with the passageways 38 of the common port 17 and a selection port 18, the passageway 44 allows fluid communication between the common port 17 and the selected selection port 18.

Still referring to FIG. 3, it is clear that the rotor seal 16 must be held firmly against the interior surface of the first end of the housing 12 in order to prevent leaking. Similarly, the front end of the rotor tip 42 must be held firmly against the interior surface of the rotor seal 16 in order to prevent leakage. Hence, the rotor 14 needs to be positioned firmly in place against the rotor tip 42 in order to allow the valve 10 to operate at pressures up to 2,000 psi or so without leaking.

Figure 4:
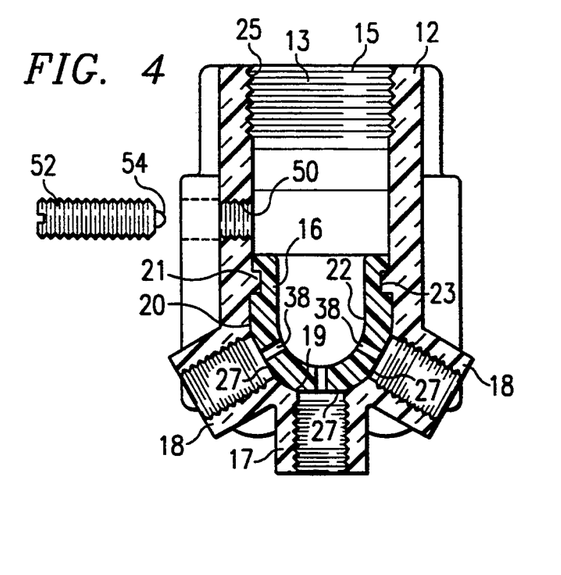
FIG. 4 is a cross-sectional view of a housing with a rotor seal in position in accordance with the present invention.

FIG. 4 illustrates the valve 10 of FIG. 3 with the rotor tip 42, rotor 14, and related elements removed. Referring now to FIG. 4, the housing 12 and the rotor seal 16 are shown. Housing 12 defines a generally cylindrical interior chamber 13 extending longitudinally from a hemisphere-shaped base 19 at its first end to an open base 15 at its opposite, second end. At its second end, the inner surface of the housing 12 has threaded grooves 25 extending downwardly from opening 15. As detailed below, the grooves 25 mate with the threads of nut 62 and help to hold the rotor 14 in place. Positioned beyond the grooves 25, the housing 12 has two protrusions 21, each of which extends into the chamber 13 from an opposite side of the housing 12. Extending through the side of housing 12 is a threaded hole 50 which intersects chamber 13. As detailed below, a detent 52 is positioned within the hole 50 in order to align and control the rotation of rotor 14.

Housing 12 is typically constructed of a durable polymer material such as polyetheretherketone, which is sold under the trademark "PEEK" and is commercially available from ICI Americas. In the preferred embodiment of the invention, the housing 12 is made of molded PEEK which is 30% by weight filled with glass or fiber glass strands or fibers. Alternatively, the housing 12 could be made of polychlorotrifluoroethylene, such as is sold under the trademark "KEL-F" and is commercially available from the 3M Company. Although somewhat difficult to machine to the precise dimensions needed in a LC system, these two materials are strong enough to allow operation of the valve 10 at pressures of up to around 2,000 psi. Moreover, these two materials can be used with most of the solvents commonly used in LC systems. Of course, a greater or lesser (or even none) amount of filler material can be used as desired. However, it is noted that other suitable biocompatible materials could be used.

Referring still to FIG. 4, the rotor seal 16 has a generally U-shaped cross-section, with an inner surface 22 and an outer surface 20. The outer surface 20 has flattened portions 27 which correspond to the shape of and are positioned adjacent to the bottoms of the common and selection ports 17 and 18. The outer surface 20 of the rotor seal 16 has recesses 23 which mate with the corresponding protrusions 21 of the housing 12. The protrusions 21 secure the rotor seal 16 in housing 12 and help prevent the rotor seal 16 from moving either radially or longitudinally within the chamber 13 of the housing 12. As noted above, a plurality of passageways 38 extend through rotor seal 16; the passageways 38 are designed and positioned so that they are aligned with the bottoms of the corresponding common and selection ports 17 and 18.

The rotor seal 16 is preferably made of a resilient material which is flexible enough to allow rotor seal 16 to have sufficient flex to press against rotor tip 42 and create a seal. At the same time, however, rotor seal 16 must be rigid enough to maintain its shape and retain a seal between it and the interior surface of the chamber 13 of the housing 12. Importantly, the rotor seal 16 must be able to meet these requirements at operating pressures of up to 2,000 psi or so. For best results, I prefer to use a rotor seal 16 made of polychlorotetrifluoroethylene, which is commercially available under the trademark "KEL-F" from the 3M Company. Another suitable alternative is polytetrafluoroethylene, which is sold under the trademark "TEFLON" and is commercially available from Du Pont. Both of these materials have the advantage of providing a high degree of chemical inertness and therefore biocompatibility; both are also inert to most of the common solvents used in LC applications. It will be obvious to those skilled in the art, however, that other suitable materials could be used.

As shown in FIG. 4, housing 12 has a threaded bore 50 which extends from the outer surface of housing 12 into the chamber 13 defined by the housing 12. Shown adjacent the housing 12 (i.e., before assembly) is a detent 52. The detent 52 is designed so that it can be threaded into the bore 50 until its tip protrudes into the chamber 13. The tip of the detent 52 has a retractable, spring-loaded ball 54 therein. As described below, the ball 54 of the detent 52 presses against and is adjacent to a neck 46 of the rotor 14. When the rotor tip 42 (and hence the rotor 14) is aligned with an appropriate selection port 18, the ball 54 extends into a detent notch 48 in the neck 46, thus holding and controlling the rotation of the rotor 14.

Given the higher pressures at which the valve 10 is to operate, it can be seen that it is important to ensure a strong seal between the rotor seal 16 and the interior surface of the housing 12. This can be accomplished by forming the housing 12 around the rotor seal 16, such as by injection molding. By molding the housing 12 around the rotor seal 16, the fluid material (which cools to form housing 12) contacts and adheres to the outer surface 20 of the rotor seal 16, thus ensuring a strong seal between housing 12 and the rotor seal 16.

Figure 5A:
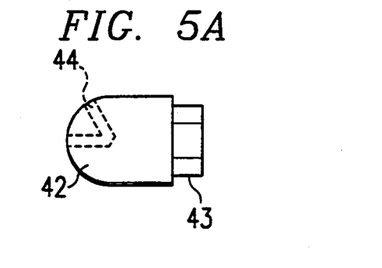
FIG. 5A is a side view of the preferred embodiment of the rotor tip.
Figure 5B:
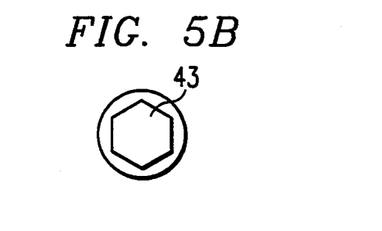
FIG. 5B is an end view of the preferred embodiment of the rotor tip.

Referring now to FIGS. 5A and 5B, the rotor tip 42 is shown in additional detail. Referring first to FIG. 5A, a side view of the rotor tip 42 is provided. Its first or front end is hemisphere-shaped. At the second end of the rotor tip 42 is a hexagonal base 43. FIG. 5B shows the rear view of the rotor tip 42, in which the hexagonal base 43 can be seen more clearly. As discussed below, this hexagonal base 43 fits into and mates with the front end of the rotor 14. The rotor tip 42 is preferably made of polytetrafluoroethylene, such as is commercially available under the trademark "TEFLON" from Du Pont. For best results, I prefer to use a rotor tip 42 which is made of polytetrafluoroethylene which is 15% by weight filled with graphite. Of course, greater or lesser (or even no) graphite may be used. Moreover, other suitable materials could be used.

Figures 6A, 6B, 7A, 7B:
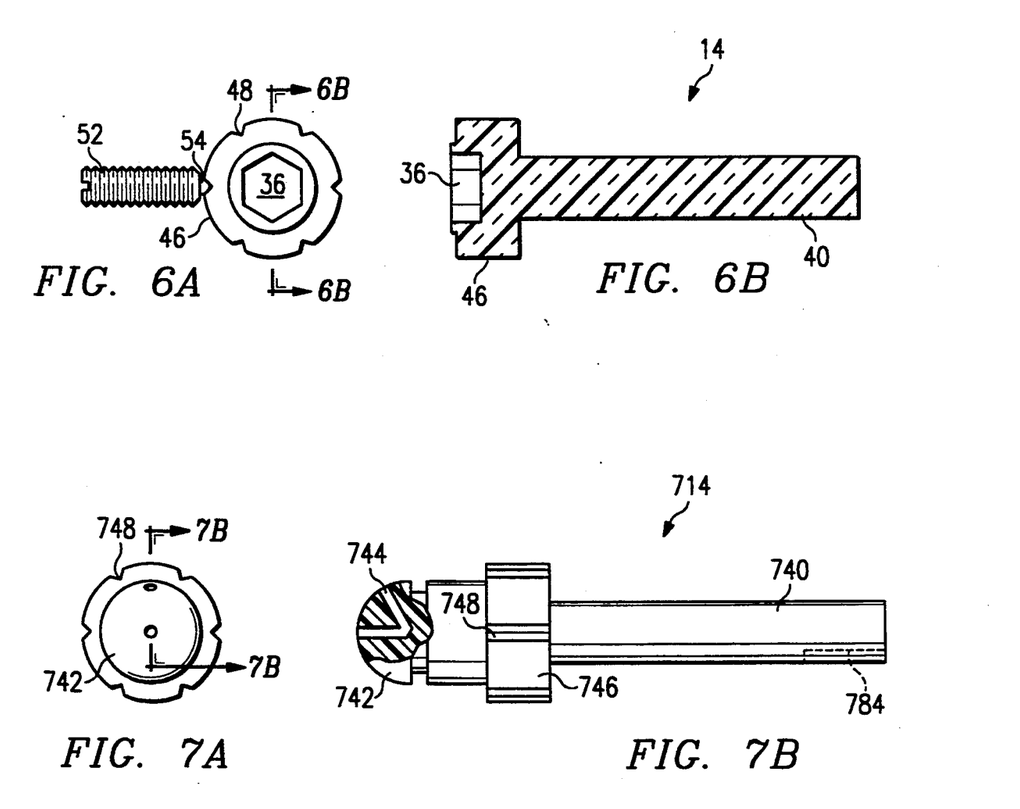
FIG. 6A is a frontal view of the preferred embodiment of the rotor and also the detent.
FIG. 6B is a cross-sectional view of the rotor and rotor tip taken along line 6B—6B.
FIG. 7A is a frontal view of an alternative embodiment of the rotor tip.
FIG. 7B is a side view (with a partial cross-sectional view along line 7B—7B) of an alternative embodiment of the rotor and rotor tip.

The rotor 14 is shown in additional detail in FIGS. 6A and 6B. FIG. 6A is a frontal view of the rotor 14, while FIG. 6B is a sectional view taken along line 6B—6B. As shown in FIG. 6B, the front end of the rotor 14 has a hexagonal seat 36 for removably holding the hexagonal base 43 of the rotor tip 42 (which was shown in FIGS. 5A and 5B). The rotor 14 also has a neck 46. The neck 46 is generally circular. As shown in FIG. 6A, the neck 46 has a number of detent notches 48, each of which corresponds to a given selection port 18. Detent notches 48 are of a suitable size so that the retractable ball 54 of the detent 52 (shown in FIG. 4) extends into each notch 48 when valve 10 is assembled and the rotor 14 is aligned so as to allow fluid communication between the common port 17 and one of the selection ports 18.

Still referring to FIG. 6B, the rotor 14 has a rotor shaft 40. As discussed below (and shown in FIG. 11), a knob 82 is attached to rotor 14 by way of a set screw 90 to prevent knob 82 from moving separately from rotor 14. This allows an operator to turn the rotor 14 by turning the knob 82.

The rotor 14 is preferably made of polyetheretherketone, which is sold under the trademark "PEEK" and is commercially available from ICI Americas. For best results, I prefer to use a rotor 14 which is made of PEEK and which is 30% by weight filled with glass or fiberglass fibers or strands. As noted above, this material thus gives rotor 14 the strength to withstand higher pressures. At the same time, however, PEEK is biocompatible and can be used with most of the solvents commonly used in LC systems. It will be obvious to those skilled in the art that other suitable materials could be used for rotor 14.

Referring now to FIGS. 7A and 7B, an alternative embodiment of the rotor tip 42 and rotor 14 is shown. In this embodiment, a unitary piece provides both a rotor tip 742 and a rotor 714. As shown in FIGS. 7A and 7B, the rotor 714 is attached to a rotor tip 742; they constitute a single piece. The rotor tip 742 includes a passageway 744 therethrough for selectively allowing fluid communication between the common port 17 (not shown in FIGS. 7A and 7B) and a selection port 18 (also not shown in FIGS. 7A and 7B).

Still referring to FIGS. 7A and 7B, the rotor 714 has a neck 746. The neck 746 has six detent notches 748, which cooperate with the retractable ball 54 in the detent 52 (not shown in FIGS. 7A and 7B) in the manner noted above to control the rotation of the rotor 714. In the alternative embodiment shown in FIGS. 7A and 7B, the rotor tip 742 is made of the same material as rotor 714. A notch 784 at the end of the rotor shaft 740 opposite the rotor tip 742 is provided to mate with a set screw 90. For best results, I prefer to use a rotor tip 742 and a rotor 714 which are made of polyetheretherketone, a plastic which is sold under the trademark "PEEK" and is commercially available from ICI Americas. It will be obvious to those skilled in the art, however, that other suitable materials could be used.

Figure 8A:
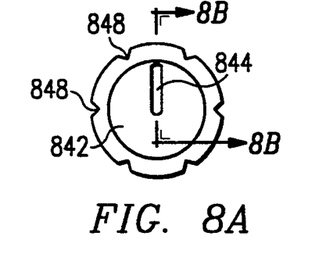
FIG. 8A is a frontal view of an alternative embodiment of the rotor tip.
Figure 8B:
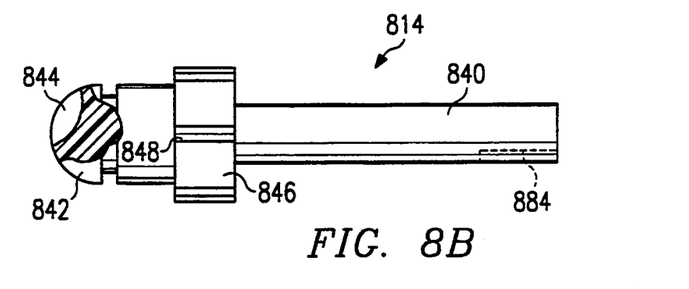
FIG. 8B is a side view (with a partial cross-sectional view along line 8B—8B) of an alternative embodiment of the rotor and rotor tip.

Another alternative embodiment of a combination of the rotor tip 42 and rotor 14 is shown in FIGS. 8A and 8B. In this alternative embodiment, rotor tip 842 and rotor 814 are essentially the same as rotor tip 742 and rotor 714, respectively. The key difference between them, however, is that rotor tip 842 has a groove 844 (instead of a passageway therethrough) which, when properly aligned by an operator, allows fluid communication between the common port 17 and the selectively chosen selection port 18.

Figure 9A:
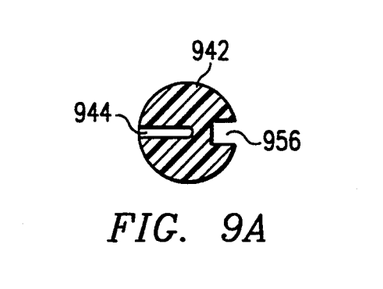
FIG. 9A is a cross-sectional view of an alternative embodiment of a rotor ball in accordance with an alternative embodiment of the present invention.
Figure 9B:
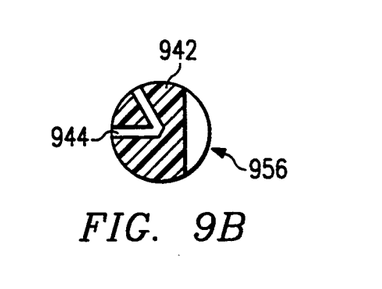
FIG. 9B is another cross-sectional view of the alternative embodiment of the rotor ball, showing FIG. 9A as rotated by 90°.
Figures 10A, 10B, 10C:
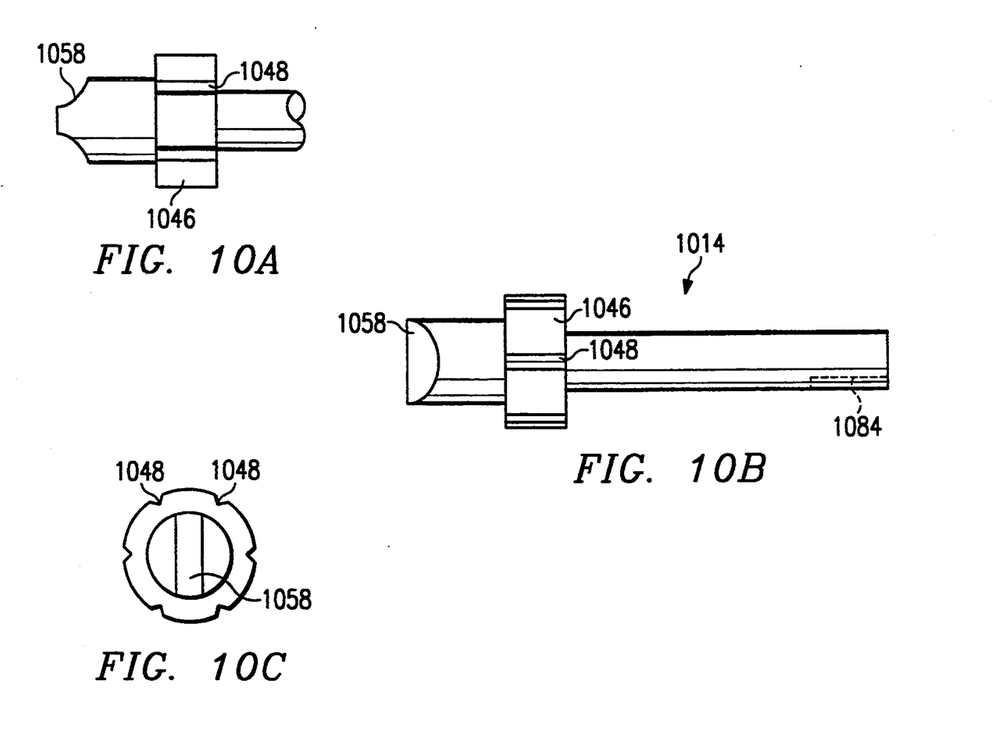
FIG. 10A is a side view of an alternative embodiment of a rotor (without a rotor ball) in accordance with the present invention.
FIG. 10B is a rotated side view of the alternative embodiment of the rotor (without the rotor ball) showing the ridge for connecting a rotor ball in accordance with the present invention.
FIG. 10C is a frontal view of the alternative embodiment of the rotor (without the rotor ball) in accordance with the present invention.

Still another alternative embodiment of a rotor tip and rotor is shown in FIGS. 9A, 9B, and 10A–C. As shown in FIGS. 9A and 9B, the rotor tip 942 can be generally spherical in shape with a groove 956 and a passageway 944 therethrough. In this embodiment, a rotor 1014 of the type shown in FIGS. 10A, 10B, and 10C is appropriate. As can be seen, the rotor 1014 is generally similar to rotor 814, rotor 714, and rotor 14. The key difference shown in FIGS. 10A–10C is that rotor 1014 includes a ridge 1058 which is designed to mate with the groove 956 in the rotor tip 942 (as shown in FIG. 9A). The rotor tip 942 can be removably attached to the ridge 1058 of the rotor 1014 by pressing the rotor tip 942 onto the rotor 1014 until groove 956 slides over and onto ridge 1058. In this alternative embodiment, rotor tip 942 can be of a different material than rotor 1014. For example, rotor 1014 as described above is preferably made of polyetheretherketone which is sold under the trademark "PEEK" and is commercially available from ICI Americas, while rotor tip 942 is made of a precision ceramic material which is commercially available from Imetra of Elmsford, N.Y. It will be obvious to those skilled in the art, however, that other suitable materials could be used.

Now referring back to FIG. 3, it can be seen that there are two possible directions of fluid flow through the valve 10. Fluid can flow inwardly from a tube connected to common port 17, through passageway 38 of the rotor seal 16, and through the aligned passageway 44 in rotor tip 42 and then out of the valve 10 through a passageway 38 in the selection port 18 chosen. Alternatively, fluid can flow inwardly from a selection port 18, through the passageway 38 aligned with that selection port 18, through passageway 44 and then outwardly through a passageway 38 aligned with the common port 17.

Referring now to FIG. 3, an additional discussion of the assembly and operation of the valve 10 is provided. Rotor 14 is held in position within housing 12 by retaining nut 62. When the rotor 14 is positioned in the housing 12 so that the rotor tip 42 presses against rotor seal 16, a portion of rotor shaft 40 extends beyond the base 15 (shown in FIG. 4) of the housing 12. Retaining nut 62 has a bore 66 through its entire body allowing retaining nut 62 to be positioned on that portion of the rotor shaft 40 extending beyond the base 15 (shown in FIG. 4) of the housing 12. Retaining nut 62 also has exterior threads 64 for mating with the threaded grooves 25 of housing 12. Retaining nut 62 is screwed into the threaded grooves 25. Positioned around rotor shaft 40 and adjacent neck 46 of rotor 14 is a thrust bearing assembly 60. As shown, the thrust bearing assembly 60 is located between one side of the neck 46 of rotor 14 and the front end of the retaining nut 62. Thrust bearing assembly 60 aids in the rotation of rotor 14 relative to housing 12 by taking up the axial load exerted on rotor 14 by retaining nut 62. Thrust bearing assembly 60 is comprised of a first plate 70 which abuts retaining nut 62, a second plate 72 which abuts one side of the neck 46, and a plurality of ball bearings 71 separating the plates 70 and 72, wherein ball bearings 71 are held in a spaced apart relationship disposed around rotor shaft 40 by a retaining ring 74. Ball bearings 71 allow the plates 70 and 72 to freely rotate with respect to each other. Via the use of the ball bearings 71, the thrust bearing assembly 60 reduces the torque required to turn rotor 14. As retaining nut 62 is tightened into the grooves 25 of housing 12, the tip of the retaining nut 62 presses against the first plate 70. By tightening retaining nut 62, greater axial pressure is exerted on and taken up by the ball bearings 71, which transfer the force to plate 72 and, in turn, the rotor 14. Plates 70 and 72 are essentially washers, and the ball bearings 71 and retaining ring 74 are commercially available and are easily obtained.

Referring still to FIG. 3, rotational force is exerted on rotor 14 when an operator turns a knob 82, which is attached to the end of rotor shaft 40. Knob 82 has a longitudinal bore 86 into which the end of rotor shaft 40 is inserted. Knob 82 also has a threaded radial bore 88 into which a set screw 90 can be screwed. During assembly of the valve 10, the set screw 90 is tightened into knob 82 so that the end of set screw 90 protrudes into groove 84 of the rotor shaft 40, thus securing knob 82 to rotor shaft 40. When an operator decides to choose another selection port 18, the operator turns knob 82. Knob 82 moves shaft 40, thereby causing the rotor 14 to rotate. The rotation of the rotor 14 in turn causes the rotation of rotor tip 42 and the passageway 44 therethrough. The precise alignment of the passageway 44 is maintained via the use of the detent notches 48 (not shown in FIG. 3) and the retractable ball 54 (also not shown in FIG. 3). As described above, when the rotor 14 turns, the retractable ball 54 is forced back into detent 52 by the neck 46. Rotor 14 is rotated until the next corresponding detent notch 48 on neck 46 allows the retractable ball 54 to snap back out of detent 52 and into notch 48. At this point, passageway 44 will be aligned with the next selection port 18. When the retractable ball 54 is located in a detent notch 48, it holds the rotor 14 in that current position and prevents further rotation (until an operator again turns knob 82).

Precise alignment of the passageway 44 in the rotor tip 42 and the passageways 38 in the rotor seal 16, as well as the holes in the ports 17 and 18, is accomplished as follows. As noted, the housing 12 is molded in place around rotor seal 16. After the interior surface 20 of the rotor seal 16 is finished, a rotor tip 42 and rotor 14 are inserted into the chamber 13 of the housing 12. As detailed above, rotor 14 can be aligned via the interaction of the ball 54 and the detent notches 48. A hole through the common port 17, and a corresponding passageway 38 through the rotor seal 16, is then machined. Next, a hole through the selection port with which the passageway 44 is aligned, and a corresponding passageway 38 through the rotor seal 16, is machined. At that point, the rotor tip 42 and rotor 14 can be removed from the housing 12 and then the remainder of the selection ports 18 and corresponding passageways 38 in the rotor seal 16 are machined. After cleaning, the rotor tip 42 and rotor 14 can be reinserted into the housing 12 and the assembly of valve 10 can be completed.

Figure 11:
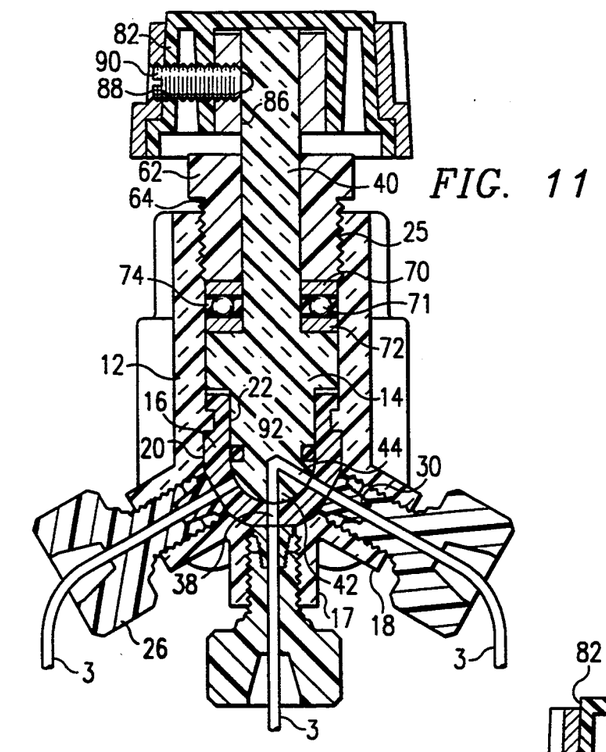
FIG. 11 is a cross-sectional view of an alternative embodiment of the multiport selection valve of the present invention.

FIG. 11 shows the valve 10 shown in FIG. 3, except that in FIG. 11, a unitary rotor 14 is used, an O-ring seal 92 is used, and tubing 3 is connected to the ports 17 and 18. As shown in FIG. 11, such a seal can be obtained by screwing a male nut 26 into a port so that a base of the ferrule 30 presses against the bottom of the ports 17 and 18. In the embodiment shown in FIG. 11, three pieces of tubing 3 are connected to the common port 17 and to two of the selection ports 18. These connections are made by using a threaded male nut 26 which mates with the threaded grooves inside the ports 17 and 18 to establish a retaining engagement. By using appropriate fittings, a leak-free seal between the base of the ferrule 30 and the housing 12 can be maintained. Such fittings as may be needed to accomplish such a seal are commercially available from Upchurch Scientific, Inc., of Oak Harbor, Wash. Additional information regarding the use of fittings in LC systems can be found in *HPLC Fittings* (2d ed. 1992), by Paul Upchurch; this booklet is incorporated by reference herein.

Referring still to FIG. 11, an O-ring seal 92 is positioned around rotor tip 42. When the first end of the rotor 14 is in position within rotor seal 16, the O-ring seal 92 forms a seal between the inner surface 22 of the rotor seal 16 and the exterior of the rotor 14. The O-ring seal 92 thus prevents any leakage that might otherwise develop during operations from somehow entering into chamber 13. Thus, O-ring seal 92 operates to contain any leaks that may develop as fluid is transferred through valve 10. Preferably, the O-ring seal 92 is made of a synthetic elastomer, such as the type which is commercially available under the trademark "KEL-REZ" from Du Pont. Alternatively, the O-ring seal 92 could be made from the synthetic elastomer sold under the trademark "CHEM-REZ," which is commercially available from Green-Tweed, or the polymer sold by DuPont under the trademark "TEFLON" (i.e., polytetrafluonethylene).

Still referring to FIG. 11, it can be seen that the diameter of passageway 44 is essentially the same as that of the tubing 3 which is connected to the ports. One orifice of passageway 44 is aligned with the tubing 3 connected to common port 17, while the other orifice is aligned with the tubing 3 connected to one of selection ports 18. When rotor tip 42 is rotated, the orifice of the passageway 44 remains aligned with common port 17, while the alignment of the other orifice of the passageway 44 is changed to that of a different selection port 18.

Figure 12:
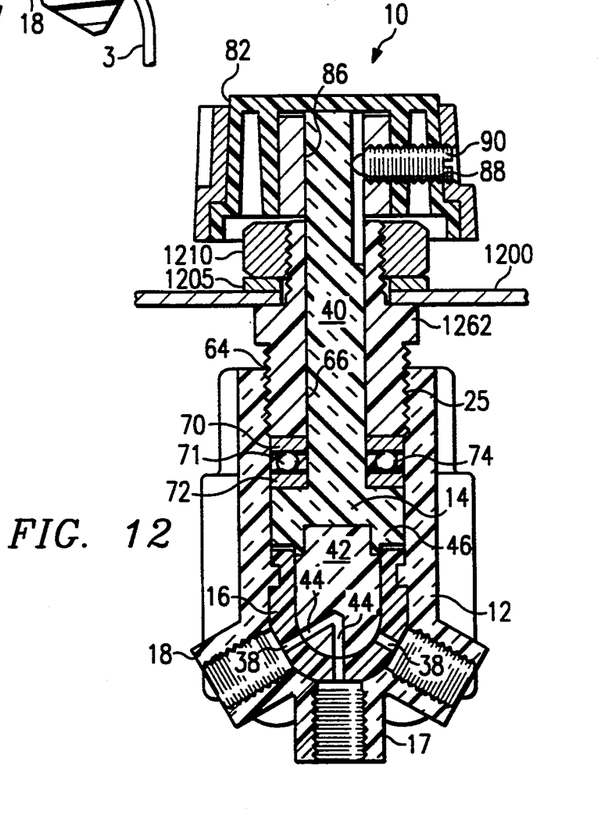
FIG. 12 is a cross-sectional view of an alternative embodiment of the multiport selection valve of the present invention.

In an alternative embodiment, a rotational force is exerted on rotor 14 through an actuator 100, as referred to in FIG. 2. Since the torque required to turn rotor 14 has been reduced by thrust bearing assembly 60 (as described above), small, electrically operated actuators 100 may be employed. In this embodiment, a motor drive apparatus (an actuator 100) is secured to rotor shaft 40 with the aid of groove 84. As is well known in the art, such an actuator can be controlled via a preprogrammed personal computer as the controller 101, thus allowing the valve 10 to be automatically controlled. FIG. 12 shows the valve 10 of FIG. 3, except that in FIG. 12, the valve 10 is attached to a bulkhead 1200 by the fastening means described below. In FIG. 12, the valve 10 includes a special retaining nut 1262 which has both a first threaded end (which is threaded into the housing 3) and a second threaded end. The valve 10 is positioned in a groove in the bulkhead 1200. Prior to attached knob 82 to the rotor 14, a washer 1205 and nut 1210 are placed onto the second end of the nut 1262 as shown. The nut 1210 is then screwed onto the threaded second end of nut 1262, securing the valve 10 to the bulkhead 1200. Knob 82 can then be attached to the rotor 14 by the use of the set screw 90 in the manner described above. In this embodiment, valve 10 can be easily incorporated into other LC equipment and components for LC systems.

While the present invention has been shown and described in its preferred embodiment and in certain specific alternative embodiments, those skilled in the art will recognize from the foregoing discussion that various changes, modifications, and variations may be made thereto without departing from the spirit and scope of the invention as set forth in the claims. Hence, the embodiment and specific dimensions, materials and the like are merely illustrative and do not limit the scope of the invention or the claims herein.

I claim the following:

1. A multiport selection valve for selectively allowing fluid communication between at least two ports comprising:
   a polymeric biocompatible housing defining a generally cylindrical interior chamber and having at a first end a common port and a plurality of selection ports;
   a rotor seal having a plurality of passageways therethrough, wherein said rotor seal is located at the first end within the chamber of said housing and sealingly engages said housing;
   a biocompatible rotor located within the chamber of said housing;
   a biocompatible rotor tip having a passageway therethrough, wherein said rotor tip is removably attached at one end thereof to a first end of said rotor and wherein said rotor tip is positioned adjacent to said rotor seal at another end thereof; and
   means for selectively aligning said rotor tip so that its passageway allows fluid communication between the common port and one of said selection ports.

2. The multiport selection valve according to claim 1 wherein said rotor tip comprises a ball which has a groove on a side thereof opposite an opening of the passageway of said rotor tips, and wherein said rotor has a ridge at its first end, wherein the ridge couples with the groove to removably attach the rotor tip to said rotor.

3. The multiport selection valve according to claim 2 wherein the rotor ball comprises a ceramic material.

4. The multiport selection valve according to claim 1 wherein said rotor has a neck with a plurality of detent notches positioned thereon and wherein said means for aligning said rotor tip comprises a detent having a retractable ball which extends into the chamber of said housing, wherein said ball engages a detent notch when the passageway of said rotor tip is aligned with one of said selection ports.

5. The multiport selection valve according to claim 4 wherein the aligning means further comprises:
   a knob attached to said rotor so that when said knob is turned, said rotor and said rotor tip also are turned.

6. The multiport selection valve according to claim 4 wherein the aligning means further comprises:
   an actuator attached to said rotor so that said actuator selectively rotates said rotor via instructions from an operator.

7. The multiport selection valve according to claim 1 wherein said housing member has threaded grooves at a second end thereof and wherein the valve further comprises a retaining nut having exterior threads and a bore therethrough, wherein said nut fits over a shaft of said rotor and wherein said retaining nut is screwed into the threaded grooves at the second end of said housing member.

8. The multiport selection valve according to claim 7 further comprising:
   a thrust bearing member positioned between the neck of said rotor and a tip of said retaining nut, wherein said thrust bearing allows said rotor to rotate more freely.

9. The multiport selection valve according to claim 8 wherein said thrust bearing comprises:
   two plates having bores through which said rotor shaft passes;
   a plurality of ball bearings positioned between said plates to allow independent rotation of said plates relative to each other; and
   a ring for securing said ball bearings between said plates.

10. The multiport selection valve according to claim 1 wherein said rotor tip comprises polytetrafluoroethylene.

11. The multiport selection valve of claim 1 wherein said rotor tip comprises a mixture of polytetrafluoroethylene and graphite.

12. The multiport selection valve according to claim 1 wherein said rotor seal comprises chlorotetrafluoroethylene.

13. The multiport selection valve according to claim 1 wherein said rotor comprises polyetheretherketone.

14. The multiport selection valve of claim 1 wherein said housing comprises a mixture of polyetheretherketone and glass fibers.

15. The multiport selection valve according to claim 1 further comprising an O-ring seal positioned around said rotor tip, wherein said O-ring seal forms a seal between said rotor tip and said rotor seal.

16. A multiport selection valve for selectively allowing fluid communication between at least two ports, comprising:
   a polymeric biocompatible housing defining a generally cylindrical interior chamber and having at a first end a common port and a plurality of selection ports;
   a biocompatible rotor seal having a plurality of passageways therethrough, wherein said rotor seal is located at the first end within the chamber of said housing and sealingly engages said housing;
   a biocompatible rotor located within the chamber of said housing, wherein said rotor has a rotor tip having means for conducting fluid and wherein the rotor tip is positioned adjacent to said rotor seal; and
   means for selectively aligning the rotor tip so that the means for conducting fluid allows fluid communication between the common port and one of said selection ports.

17. The multiport selection valve according to claim 16 wherein the means for conducting fluid comprises a passageway through the rotor tip.

18. The multiport selection valve according to claim 16 wherein the means for conducting fluid comprises a groove in the rotor tip.

19. A multiport selection valve for selectively allowing fluid communication between at least two ports, comprising:
   a biocompatible housing defining a generally cylindrical interior chamber and having at a first end a common port and a plurality of selection ports;
   a rotor seal having a plurality of passageways therethrough, wherein said rotor seal is located at the first end within the chamber of said housing and sealingly engages said housing;
   a biocompatible rotor having a first end located within the chamber of said housing, wherein said rotor has a ridge at its first end;
   a biocompatible rotor tip having a passageway therethrough, wherein said rotor tip comprises a ball having a groove on a side thereof opposite an opening of the passageway of said rotor tip, and wherein a ridge at the first end of said rotor couples with the groove of said rotor tip to removably attach said rotor tip at one end thereof to said rotor, and wherein said rotor tip is positioned adjacent to said rotor seal at another end thereof; and means for selectively aligning said rotor tip so that its passageway allows fluid communication between the common port and one of said selection ports.

20. The multiport selection valve of claim 19, wherein said rotor tip comprises a ceramic material.

21. The multiport selection valve of claim 19, wherein said rotor seal comprises a one-piece biocompatible member that has first and second ends and is oriented coaxially within the chamber, wherein said rotor seal's first end is nearer to the common and selection ports than said rotor seal's second end, and wherein the first end of said rotor seal comprises a hemispherically-shaped portion.

22. The multiport selection valve of claim 21, wherein the second end of said rotor seal comprises a circular recess extending around its outside circumference for engaging a circular boss extending around the inside circumference of the chamber of the housing member.

23. The multiport selection valve of claim 21, wherein said housing comprises an injection molding around the rotor seal.

24. The multiport selection valve according to claim 21, wherein said rotor tip and said rotor comprise a unitary piece.

* * * * *